United States Patent [19]

Dory

[11] Patent Number: 4,942,878

[45] Date of Patent: Jul. 24, 1990

[54] LOCALIZATION METHOD AND DEVICE FOR DETERMINING THE DEGREE OF FRAGMENTATION OF STONES

[76] Inventor: Jacques Dory, 91, rue des Molveaux, 77450 Coupvray, France

[21] Appl. No.: 63,570

[22] PCT Filed: Sep. 29, 1986

[86] PCT No.: PCT/FR86/00335

§ 371 Date: May 27, 1987

§ 102(e) Date: May 27, 1987

[87] PCT Pub. No.: WO87/01927

PCT Pub. Date: Apr. 9, 1987

Related U.S. Application Data

[60] Continuation-in-part of Ser. No. 37,369, Apr. 13, 1987, abandoned, which is a division of Ser. No. 728,905, Apr. 30, 1985, Pat. No. 4,658,828.

[30] Foreign Application Priority Data

Sep. 27, 1985 [FR] France .................................. 85 14330

[51] Int. Cl.⁵ ............................................ A61B 17/22
[52] U.S. Cl. .............................. 128/660.03; 128/24 A
[58] Field of Search ...................... 128/24 A, 328, 660, 128/804

[56] References Cited

U.S. PATENT DOCUMENTS 4,526,168  7/1985  Hassler et al. ................ 128/24 A X
4,669,483  6/1987  Hepp et al. .......................... 128/660

Primary Examiner—Ruth S. Smith
Attorney, Agent, or Firm—William A. Drucker

[57] ABSTRACT

The disclosure relates to apparatus for localizing the fragments of stones associated to a lithotrite comprising a spherical focussing cup acting as a power transducer and an auxiliary transducer subjected to a sectorial scanning and mounted at the center of the cup and coupled to an echography device. The apparatus comprises an auxiliary generator for exciting the power transducer with pulses generated at a frequency of a few hertz and at a power reduced with respect to that of the shootings. During the emission of the pulses with reduced power, the receiver of the echographic device is connected to an auxiliary cathode tube which forms an A echography image in order to localize the fragments of stones.

11 Claims, 1 Drawing Sheet

U.S. Patent     Jul. 24, 1990     4,942,878
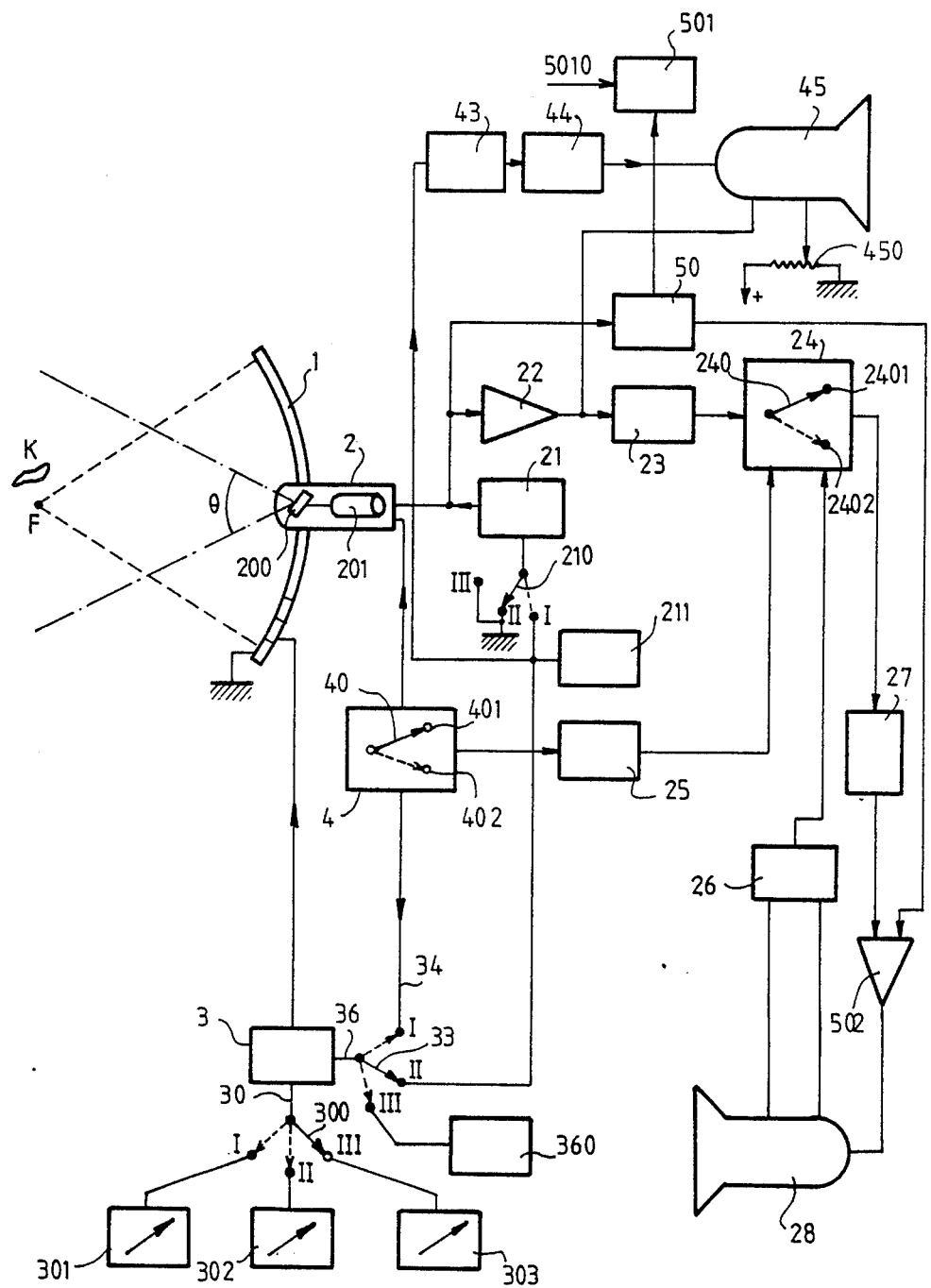

LOCALIZATION METHOD AND DEVICE FOR DETERMINING THE DEGREE OF FRAGMENTATION OF STONES

CROSS REFERENCE TO PRIOR APPLICATIONS

This application is a continuation-in-part of Ser. No. 073,369, filed Apr. 13, 1987, now abandoned which is a division of Ser. No. 728,905, filed Apr. 30, 1985 now U.S. Pat. No. 4,658,828, which claims any benefits to which it is entitled under 35 U.S.C. 120 on the basis of U.S. Pat. No. 4,617,931.

During the use of an extracorporeal lithotriptor for destroying gall stones by pressure waves, the degree of fragmentation thereof, the knowledge of which is important for determining the moment when the firing should be stopped, is somtimes difficult to assess.

In fact, from the very beginning of fragmentation, small fragments may be deposited under the stone and form a screen in front of the locating device, for example an echography device, which the lithotriptor comprises. The image which then appears on the screen of this device is that of the layer formed by the fragment which then merges with the rest of the stone. The resolution of the device is not sufficient to separate each elementary particle and the operator, deceived by the aspect of the image, may stop the treatment prematurely.

Another case of error is that in which, with the gall stone enclosed in a cavity, the fragments remain in position. The result is that the echographic image may remain unchanged even when the fragmentation is complete.

The invention has as an object a method of locating the stones and fragments thereof comprising the formation of an image and observation thereof in real time, characterized in that said fragments are subjected to pulsed and focused elastic waves emitted with a relatively small power with respect to that of the firing, but appreciably higher than that used for the echography, and at a rate of the order of a few hertz, advantageously 5 to 10 Hz and in that the shape modifications undergone by the echoes of the fragments are interpreted so as to obtain information relative to the size of the fragments.

The invention is based on the discovery that small sized fragments (less than 3 mm for example), subjected to such an elastic wave, undergo a movement of an amplitude inversely proportional to their size. Because of interference phenomena there partly results therefrom a substantial and characteristic modification of the shape of the echoes reflected by the fragment. The echo may disappear completely if the size of the fragment is less than a certain limit, it will on the other hand be stable for a fragment of a size greater than a given threshold.

In a preferred embodiment, the stone and its fragments subjected to said elastic waves are observed with type A echography effected on a line which passes through the focal spot of the elastic wave beam and the disappearance or modification of the echo are observed on each of the fragments for indicating that the above mentioned lower limit of size has been reached and that it is no longer necessary to resume firing.

In an improvement, a zone containing fragments whose sizes it is desired to analyse more finely is subject, during application of said elastic waves, to elastic examination pulses and the variation of the carrier frequency of these examination pulses by reflection from the fragments is measured so as to give an indication of the speed of movement of said fragments under the impact of said elastic waves.

The invention also has as an object a device for implementing the above mentioned process. In its preferred embodiment, this device uses the main ultrasonic pulse emitter of the lithotriptor at reduced power and at a pulse rate appropriate to setting in motion the gall stone fragments and displays the echoes in echography A.

Other characteristics, as well as the advantages of the invention, will clearly appear from the light of the following description.

The single FIGURE of the accompanying drawing is the general diagram of a lithotriptor equipped with an apparatus for locating gall stone fragments in accordance with a preferred embodiment of the invention.

A transducer 1 has been shown in the drawing in the form of a spherical skull cap, constructed and mounted so as to be able to be positioned along three orthogonal axes, as was described in U.S. Pat. No. 4,617,931, filed on Nov. 26, 1984 in the name of Jacques Dory for: "Ultrasonic pulse apparatus for destroying calculuses" and which is incorporated in the present disclosure as a part thereof. An auxiliary transducer 2 is fixed to the center of the spherical skull cap and includes an oscillating piezoelectric element 200 controlled by a motor 201, itself controlled by an electronic circuit 4.

The transducer 1 is energized by a pulse emitter 3 one input 30 of which for adjusting the peak power emitted is connected, through a switch 300, either, in position I, to a member 301 which allows said power to be regulated to a value appropriate for lithotrity (of the order of 100 Kw for example), or, in position III, to a member 300 which fixes said power at a much lower value appropriate to fragmentation location (of the order of 10 to 20 Kw for example), or finally, in position II, to a member 302 which fixes said power at a still more reduced value, of the order of a few watts. The construction of the members shown symbolically by the rectangles 301 to 303 is within the scope of a man skilled in the art. So as to obtain the power of a few watts, block 302 must cause a considerable reduction of the power supply voltage of the emitter.

The waves generated by emitter 3 have for example a high frequency of 500 KHz and are emitted, depending on whether switch 33 occupies the positions I, II or III, either as pulses of a few $\mu$s duration synchronized by circuit 4 as will be explained further on, or in the form of 256 pulses spread out over a duration of 1/10 s which corresponds to a complete oscillation of element 200, or finally in the form of brief pulses at a rate of 5 to 10 Hz.

Circuit 4 generates saw tooth voltage signals comprising successively portions of 1/10th of a second with increasing slope and portions of 1/10th of a second with decreasing slope. These portions, which control the rotation of motor 201 in one direction then in the other for providing sectorial scanning of angle $\theta$, are separated from each other by intervals of 1/100 th second during which a control is fed to output 34. Therefore, when the switch 33 is in position I, said controls are received at the synchronization input 36 of the emitter 3, which triggers off a burst of firing. On the other hand, when switch 33 is in position II the input 36 is connected to a generator 211 which delivers 256 pulses during said portions of 1/10th second. Finally, when switch 33 is in position III, the input 36 is connected to a member 360 which synchronizes the emitter to a pulse frequency of 5 to 10 Hz.

Furthermore, the generation of saw teeth by circuit 4 is controlled by a switch 40: the saw teeth are generated when this switch is in position 401, and interrupted when it is in position 402. The scanning by transducer 2 is then stopped in the median position of the beam. Simultaneously the memory 24 which receives the echoes from transducer 2, passing through an amplifier 22 and through an analog-digital converter 23, is then locked in the "read only" position, by means of a switch 240 which is coupled (in a way not shown) to switch 40 which is then in position 2402.

When switch 40 is on the other hand in position 401, switch 240 is in position 2401 and memory 24 operates for writing and reading: the signals received at 22 are stored line by line in memory 24, a writing address device 25, controlled by circuit 4, causing the respective deflection angles of the beam emitted and/or received by transducer 2 to correspond with the respective lines of the memory. A device 26 for rapid reading of the memory energizes the X and Y deflection coils of a cathode ray tube 28, so the brilliancy control electrode receives the corresponding contents of memory 24, transformed into an analog signal by a digital-analog converter 27.

Transducer 2 is connected to a very high frequency pulse emitter (5 MHz for example) 21 synchronized either by the pulse generator 211 when switch 210 is in position I, or grounded when switch 210 is in position II or III (these positions I to III being obtained at the same time as the corresponding positions of switches 33 and 300). In the positions II or III of the switches, emitter 21 is therefore not in service and transducer 2 only operates for reception when a size control pf the fragments by echography A is effected.

The signal from amplifier 22 is applied to the vertical deflection control of the beam of a second cathode ray tube 45, whose horizontal deflection control is provided by a generator 44. This latter is itself synchronized by generator 211, with an adjustable delay delivered by a delay circuit 43. Members 43 and 44 are adjusted so that a small portion only of the zone of the body containing the stone K is displayed on the screen of the cathode ray tube 45.

By way of example, if the gall stone is at a depth of 100 mm, the tube will only display a zone corresponding to a depth of 20 mm, and the delay will be adjusted so as to correspond to a distance of 90 mm travelled by the elastic waves. The zone effectively displayed will thus be limited by depths between 90 and 110 mm.

The operation of the device which has just been described is as follows:

When switches 33, 300 and 210 are in position I, high power pulses are generated by transducer 1 and focused at the center F of the sphere.

For the duration of each portion of 1/10th second, the sectorial scan echography device formed by the transducer, the auxiliary emitter and the reception, processing and display means 22 to 27, displays on the screen of the cathode ray tube 28 an image of the scanned region of the body including the kidney and the gall stone K.

Furthermore, the display device is adapted, in a way known per se, so as to materialize on the screen of the cathode ray tube (for example by a cross) the theoretical position of the focal spot in the sectional plane shown, which plane passes through the axis of symmetry of transducer 1. (As a B Scan is effected in an axial plane). The operator begins by moving transducer 1 along X until the stone appears clearly on the screen, then he moves it along Y and Z until the cross coincides with the central region of the image of the stone. At this time, the switches may be put into position II; the region of the focal spot is then made visible on the screen, with a luminosity proportional to the corresponding energy concentration. Thus a representation is obtained of what the distribution of the energy of the shock wave will be during firing, which allows the adjustments to be checked and completed.

When it is desired to check the fragmentation, the switches are moved from position I to position III and switch 40 to position 402. The result is that scanning is stopped on the median line and, with switch 240 itself in position 2402, the cathode ray tube 28 continues to display the gall stone. Moreover, transducer 1 then works at reduced power and at a rate of 5 to 10 Hz, which results in causing agitation of the stone fragments.

The echoes resulting from the reflection of the pulses emitted by transducer 1 are received by transducer 2 and are transmitted to the horizontal deflection control of the cathode ray tube 45 whose luminosity control electrode is subjected to a DC voltage adjustable by means of a potentiometer 450. Thus an echography A of the stone is obtained, on a scale such that the image of the fragments will be clearly visible. This image is also provided not only when the switches are in position I but also when they are in position III and, consequently, going over from position I to position III allows either the absence of deformation, or the deformation or even the disappearance of the image to be observed for each fragment.

During lithotrity the progressive reduction in size of the fragments may thus be monitored by making the successive switchings from I to III.

At 50 has been shown a conventional Doppler device which emits a pulsed wave of very high carrier frequency (5 MHz for example) transmitted to transducer 2 and which receives the corresponding echoes coupled by the transducer 2. When it is desired to bring this device into service, switches 33, 210 and 300 are placed in position III and scanning is stopped in the median position of the beam emitted by transducer 1, switch 40 being for this purpose in position 402.

In position III, the transducer 1 emits pulsed waves at the frequency of 500 KHz with reduced power with respect to that of the firing. The rate of these pulses is also defined by generator 360.

It is preferably arranged of this rate to be a sub multiple of the rate of the Doppler pulses: this latter being for example 5000 Hz, that of the reduced power pulses for agitating the fragments may be 5–10–20 or 50 Hz. The relative setting of the two pulse trains may then be such that a Doppler pulse arrives on the fragment at the same time as an agitation pulse.

The Doppler echoes are only received during a time interval defined by a square wave generated inside device 50 in a way known per se. This square wave is applied, as well as the signal read out from memory 24 (while switch 240 is position 2402), to a mixer 502 whose output drives the luminosity control electrode of the cathode ray tube 28. Thus, on the screen of said tube, the position of an adjustable window is materialized for selecting one or more fragments.

The low frequency Doppler signal generated by device 50, and whose amplitude is proportional to the speed of movement of agitation of the fragment, is applied to a cathode ray tube or a recorder 501, preferably at the same time as the agitation pulses (applied to the input 5010). Thus, the correlations between these two signals may be observed. The frequency of the Doppler signal is inversely proportional to the size of the fragments, which permits quantitative observation thereof, if need be by spectral analysis of the Doppler signal.

The Doppler measurement and location of the fragments by echography A may be carried out simultaneously.

It goes without saying that different modifications of detail may be made to the devices described and shown without departing from the spirit of the invention. One of the means for detecting the size of the fragments may even be omitted or else, echography A may be replaced by another image forming means in real time, for example an X ray device associated with a brilliancy amplifier.

I claim:

1. A method for non invasive fragmentation of a concretion within a region of the body of a patient, comprising the steps of:
    (a) generating, during short pulse periods, an elastic wave beam focused upon said concretion and having a predetermined high power adapted for disintegrating the concretion into fragments;
    (b) radiating a pulsed acoustical signal beam and sweeping the signal beam across said region;
    (c) detecting echoes of the acoustical signal reflected in said region and forming real time images of said region by displaying said echoes;
    (d) stopping the generation of said elastic waves and subjecting said fragments to further pulsed and focused elastic waves emitted with a power which is substantially lower than said predetermined high power and sufficient for agitating the fragments, and
    (e) radiating a further pulsed acoustic signal beam directed on the agitated fragments, detecting echoes of said further acoustic signal beam reflected by said fragments and deriving from said echoes information relative to the size of said fragments.

2. The method of claim 1, wherein the power of said further elastic wave beam does not exceed 20 kilowatts.

3. The method of claim 1, wherein the pulse frequency of said further elastic wave beam is between 5 and 50 Hz.

4. The method of claim 1, wherein said further acoustic signal beam is directed through the focal point of the focused wave beam, and an A type visual display of said echoes is effected for deriving said information.

5. The method of claim 4, wherein all steps (a) to (e) are finally stopped when said echoes disappear on said A type visual display.

6. The method of claim 1, wherein said further acoustic signal beam is generated from an electric pulsed wave having a predetermined carrier frequency and said information is derived by measuring the difference between the carrier frequency of said echoes and said predetermined carrier frequency.

7. The method of claim 6, wherein said further pulsed acoustic signal beam has a pulse frequency which is a multiple of the pulse frequency of said further elastic waves and the further pulsed signal beam and the further elastic waves are synchronized.

8. A method for non invasive fragmentation of a concretion within a region of the body of a patient, comprising the steps of:
    (a) generating, during short pulse periods, and elastic wave beam focused upon said concretion and having a predetermined high power adapted for disintegrating the concretion into fragments;
    (b) radiating a pulsed acoustical signal beam and sweeping the signal beam across said region;
    (c) detecting echoes of the acoustical signal reflected in said region and forming real time images of said region by displaying said echoes;
    (d) stopping the generation of said elastic waves and subjecting said fragments to further pulsed and focused elastic wave emitted with a power which is substantially lower than said predetermined high power and sufficient for agitating the fragments, and
    (e) radiating a further beam directed on the agitated fragments and propagating within said region, detecting the further beam after propagation thereof within said region and deriving from the propagated further beam information relative to the size of the fragments.

9. A lithotrite for focused pulsed wave disintegrating of concretion within a region of the body of a patient, said lithotrite comprising:
    (a) first means for generating, during short pulse periods, an elastic wave beam focused upon said concretion and having a predetermined high power adapted for disintegrating the concretion into fragments, said first means including a first electric pulse generator and a first focusing piezoelectric transducer coupled to said first generator;
    (b) second means for radiating a pulsed acoustic signal beam, said second means including a second electric pulse generator and a second piezoelectric transducer;
    third means connected to said second transducer for sweeping said signal beam across said region;
    (d) fourth means connected to said second transducer for receiving echoes of the acoustic signal beam reflected in said region;
    (e) fifth means for forming real time images of said region by displaying said echoes;
    (f) sixth means for substantially reducing the power and the pulse frequency of said first electric pulse generator, whereby said first means will generate further pulsed and focused elastic waves adapted for agitating the fragments,
    (g) seventh means for disconnecting said second transducer from said second pulse generator and from said third means, whereby said second transducer will receive further echoes of the further pulsed and focused elastic waves reflected by the agitated fragments and
    (h) A type visual display means for displaying said further echoes to derive information relative to the size of the fragments.

10. The lithotrite of claim 9, said lithotrite further comprising:
    (i) Doppler emitter receiver means for generating an electric pulsed wave having a predetermined carrier frequency, said Doppler emitter receiver means being coupled to said second transducer, whereby the second transducer will radiate a further pulsed acoustic signal beam directed on the agitated fragments and receive echoes of said further acoustic signal beam having a further carrier frequency which differs from said predetermined carrier frequency and (j) means for deriving from the difference between the predetermined carrier frequency and the further carrier frequency information relative to the size of the fragments.

11. The lithotrite of claim 10, wherein said electric pulsed wave beam has a pulse frequency which is a multiple of the pulse frequency of said further pulsed elastic waves and said electric pulsed wave beam and said further pulsed elastic waves are synchronized.

* * * * *